United States Patent [19]

Porte

[11] Patent Number: 5,250,261
[45] Date of Patent: Oct. 5, 1993

[54] CAM-OPERATED DOORS FOR AN INCUBATOR

[75] Inventor: Johannes J. Porte, Webster, N.Y.

[73] Assignee: Eastman Kodak Company, Rochester, N.Y.

[21] Appl. No.: 887,976

[22] Filed: May 22, 1992

[51] Int. Cl.$^5$ .................. G01N 21/00; G01N 35/00
[52] U.S. Cl. .................................. 422/63; 422/64; 422/104; 119/35; 237/14; 435/809
[58] Field of Search .................. 422/63, 64, 104; 119/35; 435/809; 237/14

[56] References Cited

U.S. PATENT DOCUMENTS

| | | | |
|---|---|---|---|
| 4,298,571 | 11/1981 | DiFulvio et al. | 422/65 |
| 4,356,967 | 11/1982 | Lunick | 237/14 |
| 4,622,457 | 11/1986 | Bradley et al. | 235/464 |
| 5,034,191 | 7/1991 | Porte | 422/64 |
| 5,089,229 | 2/1992 | Heidt et al. | 422/64 |

FOREIGN PATENT DOCUMENTS 61-209341 9/1986 Japan.

*Primary Examiner*—James C. Housel
*Assistant Examiner*—N. Bhat
*Attorney, Agent, or Firm*—Dana M. Schmidt

[57] ABSTRACT

An incubator housing is disclosed with access apertures and doors, and a single mechanism for operating the doors comprising a cam, a cam track, and a cam follower on each door mounted in the track.

2 Claims, 2 Drawing Sheets

CAM-OPERATED DOORS FOR AN INCUBATOR

FIELD OF THE INVENTION

The invention relates to a mechanism for controlling access to an incubator, preferably by a single drive means.

BACKGROUND OF THE INVENTION

It is conventional in incubators for analyzers, to provide access apertures, e.g., in the top thereof, for accessing the interior of the incubators for whatever function is needed. Doors are commonly mounted, one for each aperture, with activation means for opening and closing the access aperture. For example, in the incubators of Japanese Kokai 61/209341, an access aperture in the top of the housing is closed and opened by a door that is pivoted by a motor. Thus, for each such aperture, a separate door and a separate means for operating the door are provided. The doors are normally closed to control the environment of the incubator.

Instead of having separate drive means for each of said doors, and a timing program to coordinate such plural drive means, it would be advantageous to have a driving mechanism that will automatically drive all the doors from a single motor.

SUMMARY OF THE INVENTION

The invention provides a solution to the problem of having one motor drive plural incubator doors at different locations.

More specifically, there is provided an incubator comprising a plurality of stations each constructed to hold an assay for incubation at a controlled temperature, a housing enclosing the stations, means for adjusting the temperature within the housing, at least one aperture in the housing for providing access to the stations, and door means for opening and closing each at least one aperture automatically in response to a signal, the door means including a movable door for each aperture. The incubator is improved in that the door means further comprise a cam, a cam follower on each door that engages the cam, and means for rotating the cam about an axis in response to a signal to cause a door to open or close its respective aperture.

Accordingly, it is an advantageous feature of the invention that all the doors of the incubator are operated by a single drive motor, preferably by a simple mechanical linkage using a cam.

Other advantageous features will become apparent upon reference to the detailed Description of the Preferred Embodiments, when read in light of the attached drawings.

DESCRIPTION OF THE PREFERRED EMBODIMENTS

The invention is hereinafter described in connection with the preferred embodiments, in which the incubator has three doors that cover access apertures for cuvette injection, patient sample injection, and reagent injection, for a wet assay processed in a single rotor. In addition, the invention is useful regardless of the number of doors involved, of what is injected into the incubator when a door is open, and regardless of whether it is a liquid assay or a dry slide element assay or the number of rotors present.

Figure 1:
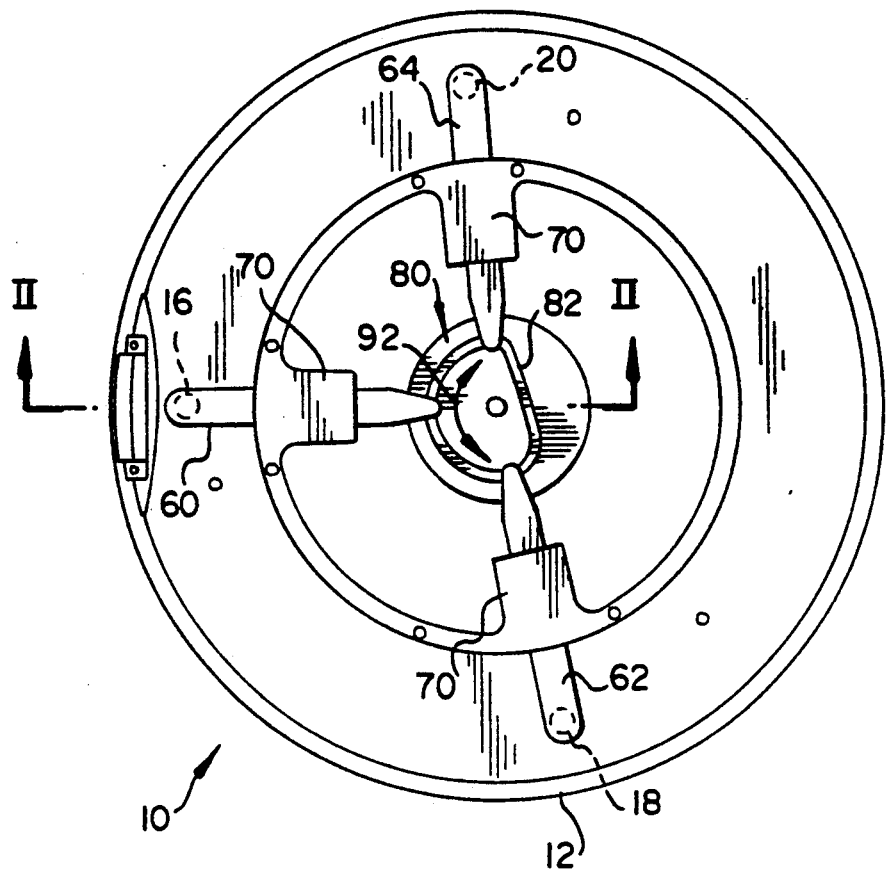
FIG. 1 is a plan view of an incubator housing, showing doors constructed in accordance with the invention.
Figure 2:
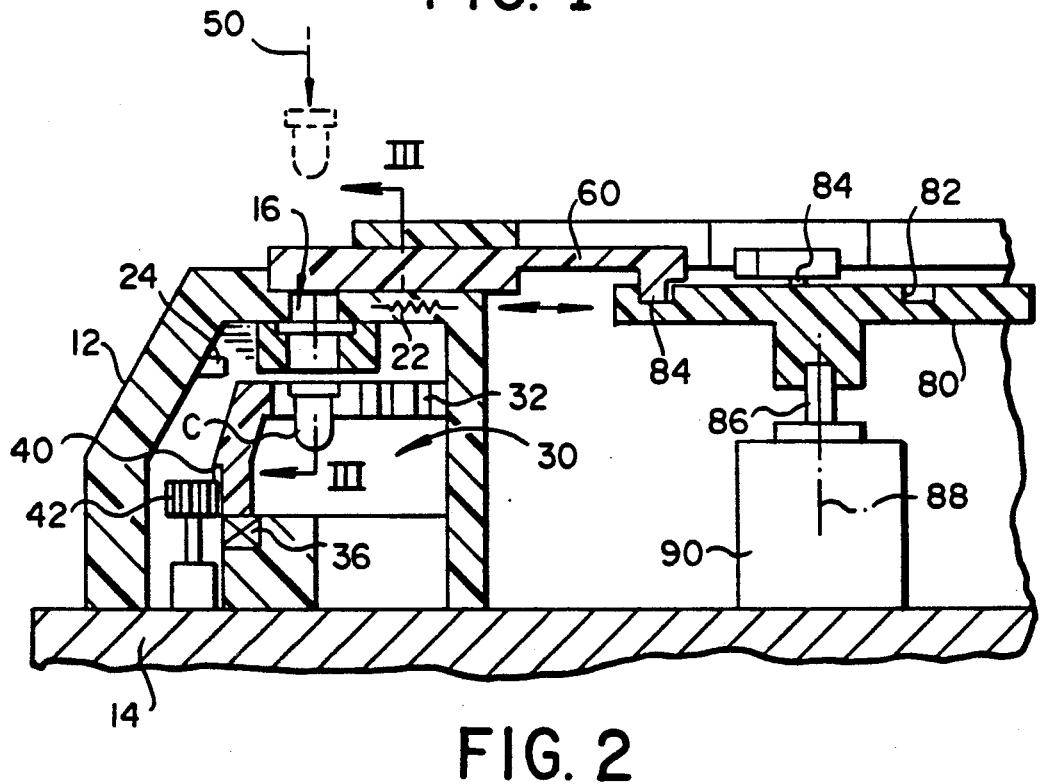
FIG. 2 is a fragmentary section view taken generally along the line II—II of FIG. 1.
Figure 3:
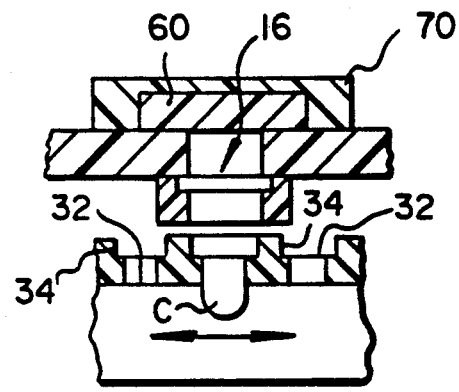
FIG. 3 is a fragmentary section view taken generally along the line III—III of FIG. 2.

As shown in FIGS. 1 and 2, an incubator 10 in a clinical analyzer comprises a housing 12 on a floor 14, FIG. 2, the housing having as is conventional several access apertures 16, 18 and 20, FIG. 1, preferably provided in the top surface of the incubator housing. (Alternatively they can be located elsewhere.) Also as is conventional, incubator 10 includes heating elements 22, e.g., in the housing as shown in FIG. 2, or adjacent, and a temperature sensor, e.g., thermistor 24, to sense and control the temperature of the incubator, and a rotor 30 for holding patient sample and reagents for incubation. Preferably, the assay is a wet assay, so that rotor 30 has slots 32, FIG. 3, to accommodate cuvettes C on rails 34, the slots opening inwardly, FIG. 2, for example, to allow movement of cuvettes C off the rotor, by a mechanism not shown. Rotor 30 is mounted for rotation by any suitable mechanism, e.g., bearings 36, FIG. 2, a rack gear 40 being provided on the outside of the rotor for engagement by a drive mechanism, e.g., pinion gear 42 as shown (or a toothed belt drive).

Preferably, access aperture 16 is used to drop in individual cuvettes "C", arrow 50, FIG. 2, whereas aperture 18 is used to add patient sample and aperture 20 to add reagent, in both cases by the use of two different aspirate and dispense devices (not shown and conventional). Each aperture is disposed so that it is vertically above where a cuvette C is located by rotor 30.

To help control the environment of incubator 10, a door 60, 62 and 64 is provided for each aperture 16, 18 and 20, FIG. 1, respectively. Most preferably, the doors are mounted for reciprocation in door frames 70, FIG. 3. Alternatively, other mechanisms can be used to slide the doors within a frame.

Figure 4:
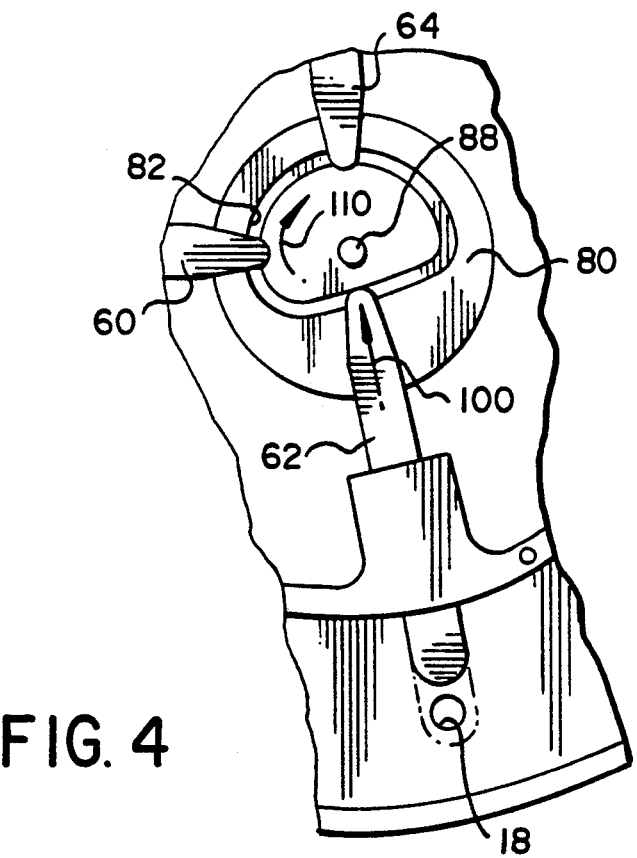
FIG. 4 is a fragmentary plan view similar to that of FIG. 1, but showing one of the three doors in its open position.

In accordance with the invention, the operation and control of any one door, and preferably all of them together, is via a mechanical linkage comprising a cam 80, FIG. 1, having a cam track 82 and a cam follower 84 on each door that engages track 82, FIG. 2. Cam 80 is mounted on a drive shaft 86 that is preferably centered on the cam at its axis 88, and shaft 86 is in turn operated by a conventional motor 90 in accordance with commands from a computer (not shown). Because track 82 is shaped to be eccentric with respect to axis 88, rotation of cam 80, arrow 92, FIG. 1, induces the doors to individually open and close by sliding within the frame. E.g., when cam 80 is in the position shown in FIG. 4, only door 62 advances towards axis 88 so that aperture 18 is opened, arrow 100, to allow patient sample to be injected into a cuvette that is underneath aperture 18. Further rotation in the direction of arrow 110 will open door 60 while door 62 is open, and then door 62 shuts. Still further rotation opens door 64, and further rotation closes door 60. Finally, door 64 shuts when track 82 is back in the position shown in FIG. 1.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In an incubator comprising a plurality of stations each constructed to hold an assay for incubation at a controlled temperature, a housing enclosing said stations, means for adjusting the temperature within the housing, a plurality of apertures in said housing for providing access to said stations, and door means for opening and closing each at least one aperture automatically in response to a signal, said door means including a movable door for each aperture;

the improvement wherein said door means further comprise a door for each of said apertures, a cam, said cam including a cam track constructed along a path that is eccentric to said axis, a cam follower on each said door that engages said cam in said cam track, and means for rotating said cam about an axis in response to a signal to cause a door to open or close its respective aperture, said track being shaped and connected to said cam followers so that only one of said cam followers and its respective door is moved away from its aperture at any one point in time.

2. An incubator as defined in claim 1, wherein said enclosure further includes guide means for causing each said door to slide relative to its aperture to close or open it.

* * * * *